United States Patent
Kitamura et al.

(10) Patent No.: US 9,056,820 B2
(45) Date of Patent: Jun. 16, 2015

(54) ALICYCLIC ALCOHOL

(75) Inventors: Mitsuharu Kitamura, Kurashiki (JP);
Yoshiharu Ataka, Wakayama (JP);
Kazuyuki Fukuda, Tokyo (JP)

(73) Assignee: Mitsubishi Gas Chemical Company, INC., Tokyo (JP)

( * ) Notice: Subject to any disclaimer, the term of this patent is extended or adjusted under 35 U.S.C. 154(b) by 0 days.

(21) Appl. No.: 13/977,274

(22) PCT Filed: Dec. 27, 2011

(86) PCT No.: PCT/JP2011/080148
§ 371 (c)(1),
(2), (4) Date: Sep. 4, 2013

(87) PCT Pub. No.: WO2012/090976
PCT Pub. Date: Jul. 5, 2012

(65) Prior Publication Data
US 2013/0338403 A1 Dec. 19, 2013

(30) Foreign Application Priority Data
Dec. 28, 2010 (JP) ................................ 2010-292938

(51) Int. Cl.
| | | |
|---|---|---|
| *C07C 31/135* | (2006.01) | |
| *C11B 9/00* | (2006.01) | |
| *C07C 29/147* | (2006.01) | |
| *C07C 53/44* | (2006.01) | |
| *C07C 35/08* | (2006.01) | |
| *C07C 29/149* | (2006.01) | |
| *C07C 51/58* | (2006.01) | |
| *C07C 67/14* | (2006.01) | |

(52) U.S. Cl.
CPC ............... *C07C 35/08* (2013.01); *C07C 29/149* (2013.01); *C07C 31/1355* (2013.01); *C07C 51/58* (2013.01); *C07C 67/14* (2013.01); *C07C 2101/14* (2013.01); *C11B 9/0034* (2013.01)

(58) Field of Classification Search
CPC .. C07C 31/1355; C07C 53/44; C07C 29/149; C07C 31/135; C07C 29/147; C07C 2101/14; C11B 9/0034
USPC .......................................... 568/826, 825, 822
See application file for complete search history.

(56) References Cited

U.S. PATENT DOCUMENTS

| | | | |
|---|---|---|---|
| 3,993,604 | A | 11/1976 | Thomas et al. |
| 5,104,851 | A | 4/1992 | Fujikura et al. |
| 2009/0163733 | A1 | 6/2009 | Joulain et al. |

FOREIGN PATENT DOCUMENTS

| | | | |
|---|---|---|---|
| JP | 50 35351 | | 4/1975 |
| JP | 1 207251 | | 8/1989 |
| JP | 1 207252 | | 8/1989 |
| JP | 7 118119 | | 5/1995 |
| JP | 9 328451 | | 12/1997 |
| JP | 2000 34243 | | 2/2000 |
| JP | 2001 31608 | | 2/2001 |
| JP | 2007 537211 | | 12/2007 |
| JP | 2009 149577 | | 7/2009 |
| JP | 2010215529 | A * | 9/2010 |
| WO | WO 2011002044 | A1 * | 1/2011 |

OTHER PUBLICATIONS

Nagasawa et al. JP2010215529A (English translation).*
JP 2010215529 A (English translation).*
JP 200034243 (machine translated English Abstract).*
JP 2001 31608 (machine translated English Abstract).*
JP 2009 149577 (machine translated English Abstract).*
JPH07118119 (machine translated English Abstract).*
JPH01207252 (machine translated English Abstract).*
JPH09328451 (machine translated English Abstract).*
WO 2011002044 A1, Jan. 2011; pp. 1-14.*
U.S. Appl. No. 13/977,221, filed Jun. 28, 2013, Kitamura, et al.
International Search Report Issued Feb. 14, 2012 in PCT/JP11/080148 Filed Dec. 27, 2011.

* cited by examiner

*Primary Examiner* — Jafar Parsa
*Assistant Examiner* — Medhanit Bahta
(74) *Attorney, Agent, or Firm* — Oblon, McClelland, Maier & Neustadt, L.L.P.

(57) ABSTRACT

Provided is an alicyclic alcohol compound which can be used as a raw material for a compound perfume, and which has excellent floral-green-like aromas which are crisp and fresh; also provided are a manufacturing method for the same, and a perfume composition which contains the alicyclic alcohol compound. An alicyclic alcohol compound having a specified structure represented by chemical formula (1) has excellent floral-green-like aromas which are crisp and fresh; and a method for manufacturing the alicyclic alcohol compound represented by chemical formula (1) by reacting, in the presence of hydrogen fluoride, 1-isopropyl-4-methylcyclohexene and carbon monoxide, reacting the resulting 4-isopropyl-1-methylcyclohexane carboxylic acid fluoride with alcohol, and, after having acquired a cyclohexane carbonyl compound, reducing the cyclohexane carbonyl compound.

7 Claims, No Drawings

ALICYCLIC ALCOHOL

TECHNICAL FIELD

The present invention relates to an alicyclic alcohol compound which can be used as a raw material for compounded perfumes, a method for manufacturing the same, and a perfume composition containing said alicyclic alcohol compound.

BACKGROUND ART

It is known that some of alicyclic alcohol compounds are useful for a raw material for compounded perfumes. For example, Non-patent Document 1 discloses that Mayol having green and muguet-like fragrance, Mugetanol having muguet-like light floral fragrance, Patchone having patchouli-like woody fragrance and the like are useful as a raw material for compounded perfumes.

PRIOR ART DOCUMENTS

Non-Patent Document

Non-Patent Document 1: "Fundamentals of perfume and fragrance preparation", edited by Mototaka Nakajima, 1995, pages 141-144, Sangyo-Tosho Publishing Co., Ltd.

DISCLOSURE OF THE INVENTION

Problems to be Solved by the Invention

The object of the present invention is to provide a novel alicyclic alcohol compound having floral-green-like fragrance useful for a raw material for compounded perfumes, a method for manufacturing the same and a perfume composition containing said alicyclic alcohol compound.

Means for Solving the Problems

As a result of synthesizing various compounds and studying fragrances thereof, the present inventors have found that the alicyclic alcohol compound represented by the following chemical formula (1) which is a novel compound has excellent floral-green-like fragrance with a crisp and fresh feeling.

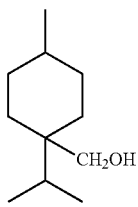

(1)

That is, the present invention relates to a novel alicyclic alcohol compound, a method for manufacturing the same and a perfume composition containing said alicyclic alcohol compound, as follows:

[1] An alicyclic alcohol compound represented by chemical formula (1).
[2] A perfume composition containing an alicyclic alcohol compound represented by chemical formula (1).
[3] A method for manufacturing an alicyclic alcohol compound represented by chemical formula (1) by reacting, in the presence of hydrogen fluoride, 1-isopropyl-4-methylcyclohexene represented by chemical formula (2) with carbon monoxide, reacting the resulting 4-isopropyl-1-methylcyclohexane carboxylic acid fluoride represented by chemical formula (3) with alcohol to obtain a cyclohexane carbonyl compound represented by general formula (4), and reducing the cyclohexane carbonyl compound represented by general formula (4) to obtain said alicyclic alcohol compound represented by chemical formula (1),

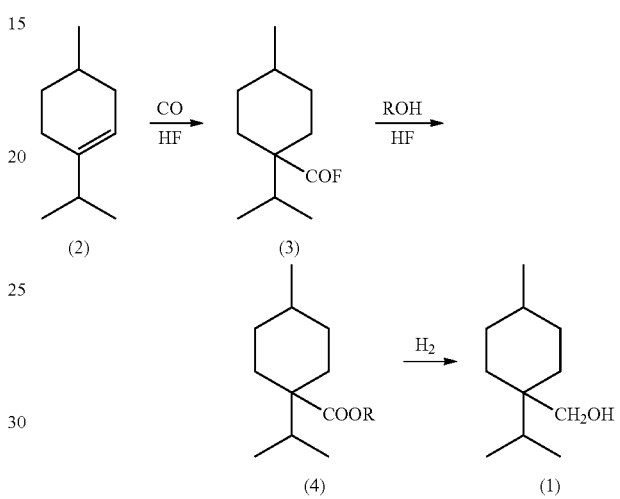

wherein "R" represents an alkyl group having 1-4 carbon atoms.

Effect of the Invention

The novel alicyclic alcohol compound of the present invention is novel in terms of having excellent floral-green-like fragrance with a crisp and fresh feeling. Because of its excellent fragrance sustaining properties, it is useful as a perfuming ingredient for a wide variety of products such as toiletry products, soaps and detergent for clothing.

In addition, the manufacturing method for producing the alicyclic alcohol compound of the present invention enables to produce said alicyclic alcohol compound by an industrially beneficial process.

MODES FOR CARRYING OUT THE INVENTION

Novel Alicyclic Alcohol Represented by Chemical Formula (1):

The novel alicyclic alcohol compound of the present invention is represented by chemical formula (1). According to the structure represented by chemical formula (1), a cis isomer and a trans isomer can be existed depending on the substitution formation of 1-position and 4-position of the cyclohexane ring. As for the structure of the novel alicyclic alcohol compound of the present invention, a cis isomer or a trans isomer can be used independently, or a mixture thereof can be used.

The novel alicyclic alcohol compound represented by the above chemical formula (1) has excellent floral-green-like fragrance with a crisp and fresh feeling, and can be used, independently or in combination with other components, as a perfuming ingredient for soap, shampoo, rinse, detergent, cosmetics, spray products, aromatic substances, perfumes, bath additives and the like.

Perfume Composition:

The perfume composition of the present invention can be obtained by combining the novel alicyclic alcohol compound represented by chemical formula (1) with other perfume components conventionally used and/or compounded perfumes having desired composition. The combination ratio depends on the types of compounded perfumes, the types and strength of intended fragrance, or the like. It is preferable to combine the novel alicyclic alcohol compound in an amount of 0.01 to 90% by mass, more preferably in an amount of 0.1 to 50% by mass.

Examples of fragrance materials which can be combined with the novel alicyclic alcohol compound of the present invention include natural essential oils, natural extracts and synthetic perfumes of hydrocarbons, alcohols, phenols, esters, carbonates, aldehydes, ketones, acetals, ethers, nitryls, carboxylic acids, lactones or the like.

Method for Manufacturing Novel Alicyclic Alcohol:

The method for manufacturing the novel alicyclic alcohol compound of the present invention comprises (a) a process of reacting a monoene compound represented by chemical formula (2) with carbon monoxide in the presence of hydrogen fluoride (hereinafter, "HF") to obtain acid fluoride represented by chemical formula (3) (hereinafter, "carbonylation process"), (b) a process of reacting the resulting acid fluoride with alcohol to obtain a cyclohexane carbonyl compound represented by general formula (4) (hereinafter, "esterification process"), and (c) a process of reducing the resulting cyclohexane carbonyl compound to obtain the alicyclic alcohol compound represented by chemical formula (1) (hereinafter, "carbonyl group-reduction process").

<(a) Carbonylation Process>

The carbonylation reaction of the monoene compound is carried out in the presence of HF under pressure of carbon monoxide. Thereby, the alicyclic carbonyl compound represented by chemical formula (3) is obtained together with various by-products including other isomers.

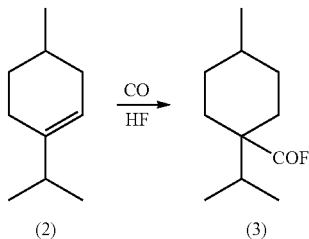

[Monoene Compound]

The monoene compound represented by chemical formula (2) can be synthesized by partial hydrogenation of a corresponding diene compound in the presence of a hydrogenation catalyst.

The monoene compound thus synthesized can be used after removing catalyst by filtration or the like and/or purifying by distillation or the like.

[Synthesis of Monoene Compound]

As the diene compounds which can be used for synthesizing the monoene compound (hereinafter, merely "diene compound"), a hydrocarbon compound having a six-membered ring structure, having only a methyl group and an isopropyl group at 1-position and 4-position respectively of the six-membered ring and having two double bonds within a molecule can be used preferably.

Examples of the diene compounds include alicyclic hydrocarbons and terpene hydrocarbons. Preferable examples thereof include limonene, α-terpinene, β-terpinene, γ-terpinene, isolimonene, α-phellandrene, β-phellandrene, Menogenes, terpinolene and dipentene. More preferable examples thereof include limonene, α-terpinene, γ-terpinene, α-phellandrene, terpinolene and dipentene. Most preferable examples thereof include terpinolene.

Hydrogenation catalysts for the diene compound are not particularly limited as long as it is commonly used for hydrogenation of unsaturated bonds. It is preferable to use a catalyst containing at least one selected from the metals belonging to 8-11 groups of the periodic table.

More specifically, it is preferable to use a catalyst containing at least one selected from the group consisting of iron, cobalt, nickel, copper, ruthenium, rhodium, palladium, silver, osmium, iridium, platinum and gold.

The hydrogenation catalyst can be a solid catalyst or a homogeneous catalyst. It is preferable to use a solid catalyst in terms of separativity from the reactant.

Examples of the solid catalysts include a non-carrying type metal catalyst and a carried metal catalyst. Preferable examples of the non-carrying type metal catalysts include (1) a Raney catalyst such as Raney nickel, Raney cobalt and Raney copper and (2) oxides of platinum, palladium, rhodium and ruthenium and a colloidal catalyst thereof.

Examples of the carried metal catalysts include a catalyst wherein at least one metal selected from the group consisting of iron, cobalt, nickel, copper, ruthenium, rhodium, palladium, silver, osmium, iridium, platinum and gold is (are) carried on or mixed with a carrier such as magnesia, zirconia, ceria, diatom earth, activated carbon, alumina, silica, zeolite and titania.

Preferable examples thereof include a carried copper catalyst wherein a copper catalyst is carried on a carrier such as a Cu—Cr catalyst (Adkins Catalyst), a Cu—Zn catalyst and a Cu—Fe catalyst, a carried platinum catalyst such as a Pt/C catalyst and a Pt/alumina catalyst, a carried palladium catalyst such as a Pd/C catalyst and a Pd/alumina catalyst, a carried ruthenium catalyst such as a Ru/C catalyst and a Ru/alumina catalyst and a carried rhodium catalyst such as a Rh/C catalyst and a Rh/alumina catalyst. Among them, it is preferable to use a catalyst containing copper in terms of reactivity and selectivity.

When a copper catalyst is used, reactivity and selectivity thereof can be improved by activating the catalyst in a solvent such as heptane at 140-200° C. under hydrogen pressure of 1-3 MPa, before subjecting to the reaction of diene compounds.

The used amount of the hydrogenation catalyst depends on the type of catalyst. It is appropriate to use the catalyst in an amount of 0.001-100% by mass, preferably 0.01-30% by mass, more preferably 0.1-20% by mass based upon the amount of the diene compound which is a raw material.

The pressure of hydrogen can be a normal pressure or an applied pressure. The pressure is usually in the range of 0.1-4.0 MPa, preferably 0.1-3.0 MPa, more preferably 0.1-2.0 MPa.

Hydrogenation reaction can be carried out in a solvent-free condition or by using a solvent. Examples of the solvents include water, organic acids such as formic acid and acetic acid; aromatic compounds such as benzene, o-dichlorobenzene, toluene and xylene; hydrocarbons such as hexane, heptane and cyclohexane; alcohols such as methanol, ethanol, isopropyl alcohol, t-butyl alcohol, ethylene glycol and diethylene glycol; ethers such as dioxane, tetrahydrofuran, dimethoxyethane and diglyme; and mixtures thereof.

The amount of solvents to be used for hydrogenation reaction is usually in the range of 0.1-30 times by mass, preferably 0.2-20 times by mass based upon the amount of the diene compound which is a raw material.

The reaction temperature of the hydrogenation reaction is usually from −90° C. to 200° C., preferably from 20° C. to 150° C., more preferably 20° C. to 100° C.

The form of hydrogenation reaction is not particularly limited as long as catalytic hydrogenation reaction can be carried out. Known methods normally employed can be employed. Examples thereof include a suspended-bed reactor wherein catalytic hydrogenation reaction is carried out by fluidizing a catalyst in fluid and a solid-bed reactor wherein catalytic hydrogenation reaction is carried out by feeding fluid whereas a catalyst is filled and fixed.

[Carbon Monoxide]

Carbon monoxide to be used for the carbonylation process of the present invention can contain inert gasses such as nitrogen and methane. The carbonylation reaction is carried out preferably under a partial pressure of carbon monoxide of 0.5-5 MPa, more preferably 1-3 MPa. When the partial pressure of carbon monoxide is 0.5 MPa or higher, the carbonylation reaction can progress sufficiently to obtain an alicyclic carbonyl compound which is a target compound in a high yield, without accompanying side reactions such as disproportionation reaction and polymerization. The partial pressure of carbon monoxide is preferably 5 MPa or lower in terms of an equipment load.

[Hydrogen Fluoride]

HF to be used for the carbonylation process is used in substantially anhydrous state, since it is used as a reaction solvent, as a catalyst and as an auxiliary material of the process. HF is used usually in an amount of 4-15 mol times, preferably 6-10 mol times to the amount of the monoene compound which is a raw material. When the molar ratio of HF is 4 mol times or more, the carbonylation reaction can progress efficiently, side reactions such as disproportionation reaction and polymerization can be inhibited and an alicyclic carbonyl compound which is a target compound can be obtained in a high yield. The used amount of HF is preferably 15 mol times or less in terms of cost of low materials and productivity.

[Reaction Conditions]

The form of the carbonylation reaction is not particularly limited and any methods such as batch reaction, semicontinuous reaction and continuous reaction can be employed.

The reaction temperature of the carbonylation reaction is preferably from to 30° C., more preferably from −40° C. to 0° C., most preferably −30° C. to −25° C. When the reaction temperature of the carbonylation reaction is 30° C. or lower or particularly −25° C. or lower, high selectivity would be achieved. It is preferable to carry out the reaction at a temperature of −50° C. or higher in terms of reaction rate.

<(b) Esterification Process>

The reaction mixture of acid fluoride produced by the carbonylation reaction is then reacted with alcohol having 1-4 carbon atoms to produce an alicyclic ester compound. At this time, it is preferable to employ a method wherein a predetermined amount of alcohol is added into the reaction mixture of acid fluoride, in terms of corrosivity of reaction apparatus.

The reaction mixture of acid fluoride produced by the carbonylation reaction (I) can be used as a raw material for the next process which is a carbonyl group-reduction process in the form of acid fluoride after distilling excess HF away and purifying by a conventional method such as distillation, or (II) can be subjected to hydrolysis to obtain a corresponding carboxylic acid compound after distilling excess HF away, and then said carboxylic acid compound can be used as a raw material for the next process which is a carbonyl group-reduction process after purifying by a conventional method such as distillation

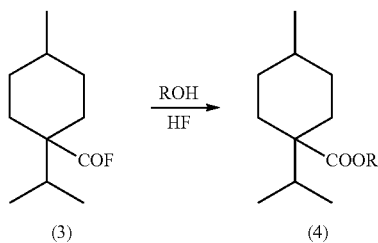

In the above chemical formula, R represents an alkyl group having 1-4 carbon atoms.

Examples of alcohols to be used for the above esterification process include methanol, ethanol, n-propanol, i-propanol, n-butyl alcohol, i-butyl alcohol and t-butyl alcohol. Among them, it is preferable to use methanol or ethanol in terms of reactivity.

Alcohol can be used in an amount of preferably 0.5-2.0 mol times, more preferably 0.8-1.5 mol times to the amount of the monoene compound which is a raw material of the carbonylation process. The molar ratio of alcohol of 0.5 mol times or more is preferable because the remaining amount of the unreacted fluoride is small and corrosion of equipment in the following processes can be inhibited. The molar ratio of alcohol of 2.0 mol times or less is preferable because dehydration reaction among alcohol molecules can be suppressed and corrosion of equipment can be inhibited.

The reaction temperature of reaction between acid fluoride and alcohol is from −40° C. to 20° C. in terms of degradation inhibition of a cyclohexane carbonyl compound represented by the general formula (4). When the reaction temperature is lower than −40° C., esterification reaction rate might become low and the yield might be decreased. When the reaction temperature is higher than 20° C., the risk of producing water as a by-product in the reaction system might be increased because of causing degradation of ester, dehydration reaction of added alcohol or the like.

The cyclohexane carbonyl compound represented by the general formula (4) thus obtained is purified by conventional methods such as distillation after distilling HF away.

<(c) Carbonyl Group-Reduction Process>

Reduction of the cyclohexane carbonyl compound represented by the general formula (4) obtained in the above esterification process can be carried out by any conventional methods for reducing a carbonyl compound to an alcohol compound, which is not particularly limited. For example, any methods shown in the Fifth Series of Experimental Chemistry, Vol. 14 (Maruzen Publishing Co., Ltd.), pages 11-27, such as hydride reduction, reduction by metal and metal salts and catalytic hydrogenation can be employed. In terms of economic efficiency, reduction by catalytic hydrogenation is preferable.

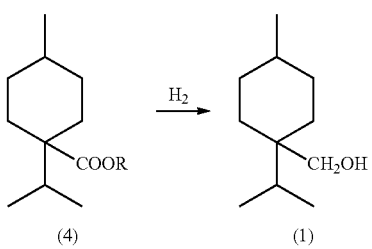

Catalysts to be used for catalytic hydrogenation of cyclohexane carbonyl compounds are not particularly limited as long as it is a normal catalyst used for hydrogenation if a carbonyl compound. It is preferable to use a catalyst containing at least one selected from the group consisting of metals belonging to 8-11 groups of the periodic table.

Particular examples thereof include a catalytic hydrogenation catalyst containing at least one selected from the group consisting of iron, cobalt, nickel, copper, ruthenium, rhodium, palladium, silver, osmium, iridium, platinum and gold.

The catalytic hydrogenation catalyst can be a solid catalyst or a homogeneous catalyst. It is preferable to use a solid catalyst in terms of separativity from the reactant.

Examples of the solid catalysts include a non-carrying type metal catalyst and a carried metal catalyst.

Preferable examples of the non-carrying type metal catalysts include (1) a Raney catalyst such as Raney nickel, Raney cobalt and Raney copper, and (2) oxides of platinum, palladium, rhodium and ruthenium and colloidal catalysts thereof.

Examples of the carried metal catalysts include a catalyst wherein at least one metal selected from the group consisting of iron, cobalt, nickel, copper, ruthenium, rhodium, palladium, silver, osmium, iridium, platinum and gold is (are) carried on or mixed with a carrier such as magnesia, zirconia, ceria, diatom earth, activated carbon, alumina, silica, zeolite and titania.

Preferable examples thereof include a carried copper catalyst wherein a copper catalyst is carried on a carrier such as a Cu—Cr catalyst (Adkins Catalyst), a Cu—Zn catalyst and a Cu—Fe catalyst, a carried platinum catalyst such as a Pt/C catalyst and a Pt/alumina catalyst, a carried palladium catalyst such as a Pd/C catalyst and a Pd/alumina catalyst, a carried ruthenium catalyst such as a Ru/C catalyst and a Ru/alumina catalyst and a carried rhodium catalyst such as a Rh/C catalyst and a Rh/alumina catalyst. Among them, it is preferable to use a catalyst containing at least one selected from the group consisting of nickel and copper in terms of reactivity.

The used amount of the catalytic hydrogenation catalyst depends on the type of catalyst. It is appropriate to use the catalyst in an amount of 1-100% by mass, preferably 3-30% by mass based upon the amount of the cyclohexane carbonyl compound which is a raw material.

[Solvent]

The carbonyl group-reduction process of the present invention can be carried out in a solvent-free condition or by using a solvent.

Examples of the solvents for the carbonyl group-reduction process of the present invention include water, organic acids such as formic acid and acetic acid; aromatic compounds such as benzene, o-dichlorobenzene, toluene and xylene; hydrocarbons such as hexane, heptane and cyclohexane; alcohols such as methanol, ethanol, isopropyl alcohol, t-butyl alcohol, ethylene glycol and diethylene glycol; ethers such as dioxane, tetrahydrofuran, dimethoxyethane and diglyme; and mixtures thereof.

Among them, it is preferable to carry out the process in a solvent-free condition or by using a solvent selected from aromatic compounds such as benzene, o-dichlorobenzene, toluene and xylene; hydrocarbons such as hexane, heptane and cyclohexane; alcohols such as methanol, ethanol, isopropyl alcohol, t-butyl alcohol, ethylene glycol and diethylene glycol; ethers such as dioxane, tetrahydrofuran, dimethoxyethane and diglyme; and mixtures thereof.

The amount of solvents in the case of using solvents for carbonyl group-reduction process of the present invention is usually in the range of 0-30 times by mass, preferably 0-20 times by mass based upon the amount of the cyclohexane carbonyl group represented by the general formula (4) obtained in the esterification process.

[Reaction Conditions]

As for the hydrogen pressure in the carbonyl group-reduction process of the present invention, it is preferable to carry out under high pressure in terms of shifting the reaction equilibrium to the alcohol side. In consideration of facility cost, the hydrogenation pressure is preferably 1-30 MPa, more preferably 2-20 MPa, most preferably 5-10 MPa.

The reaction temperature of the carbonyl group-reduction process of the present invention is preferably 100° C. or higher, more preferably 150° C. or higher, in terms of obtaining sufficient reaction rate.

The reaction temperature thereof is preferably 300° C. or lower, more preferably 280° C. or lower, most preferably 250° C. or lower, in terms of inhibiting transesterification reaction between an alicyclic alcohol to be produced and the cyclohexane carbonyl compound represented by the general formula (4).

The form of the carbonyl group-reduction process of the present invention is not particularly limited. Also in the case of carrying out by catalytic hydrogenation, it is not particularly limited as long as catalytic hydrogenation reaction can be carried out. Known methods normally employed can be employed.

Examples thereof include a suspended-bed reactor wherein catalytic hydrogenation reaction is carried out by fluidizing a catalyst in fluid and a solid-bed reactor wherein catalytic hydrogenation reaction is carried out by feeding fluid whereas a catalyst is filled and fixed.

During the reaction, alcohols having 1-4 carbon atoms are produced as by-products. The reaction can be carried out in the presence of these by-product alcohols or can be carried out by removing them continuously or intermittently during the reaction.

After removing hydrogenation catalyst from the alicyclic alcohol compound thus obtained, purification is carried out by common methods such as distillation, whereby a novel alicyclic alcohol compound represented by the formula (1) can be obtained in high purity.

EXAMPLES

The present invention will be described in more detail below, referring to Examples and Comparative Examples, which are not intended to limit the scope of the present invention.

In the Examples and Comparative Examples described below, if not otherwise specified, "%" represents "% by mass".

<Gas Chromatography Analysis>

Analyses of a monoene compound and an alicyclic alcohol compound were carried out by gas chromatography using "GC-17A", trade name, manufactured by Shimadzu Corporation, and "HR-1", trade name, manufactured by Shinwa Chemical Industries Ltd.; 0.32 mmΦ×25 m, as a capillary column. The temperature was raised from 100° C. to 250° C. at the rate of 2° C./min.

Analysis of a cyclohexane carbonyl compound was carried out by gas chromatography using "GC-17A", trade name, manufactured by Shimadzu Corporation, and "DBWAX", trade name, manufactured by J & W; 0.32 mmΦ×30 m×0.25 μm, as a capillary column. The temperature was raised from 100° C. to 250° C. at the rate of 5° C./min.

Preparation Example 1

Preparation of 1-isopropyl-4-methyl cyclohexene

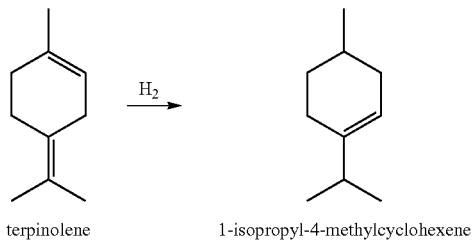

terpinolene　　　1-isopropyl-4-methylcyclohexene 50.0 g of Cu—Cr catalyst, trade name "N-203S", manufactured by JGC Catalysts and Chemicals Ltd., and 500.0 g of heptane, a special grade reagent manufactured by Wako Pure Chemical Industries, Ltd., were charged into a 5 L stainless-steel autoclave equipped with a NAC drive-type stirrer, three inlet nozzles at the top and an outlet nozzle at the bottom which has ability to regulate internal temperature by a jacket. Activation was carried out for 1 hour at 170° C. under hydrogen pressure of 2 MPa.

After cooling, 500.0 g of terpinolene, a special grade reagent manufactured by Wako Pure Chemical Industries, Ltd., was charged therein and hydrogenation reaction was carried out by stirring for 8 hours at 110° C. under hydrogen pressure of 2 MPa.

The reaction mixture thus obtained was then filtered to remove catalyst to obtain 980.0 g of a reaction mixture having the 1-isopropyl-4-methylcyclohexene concentration of 22.5%, the 4-isopropyl-1-methylcyclohexane concentration of 10.2% and the heptane concentration of 46.5%, wherein the yield was 44.2% based upon terpinolene.

After removing low boiling components by an evaporator from the reaction mixture thus obtained, rectification was carried out by a rectifier having the theoretical stage number of 20 at the distillation temperature of 118° C. under vacuum degree of 200 torr, whereby 282.0 g of a mixture having the 1-isopropyl-4-methylcyclohexene concentration of 61.6%, the 4-isopropyl-1-methylcyclohexane concentration of 31.0% with the yield based upon terpinolene of 34.8% was obtained.

Example 1

Carbonylation and Esterification of 1-isopropyl-4-methyl cyclohexene to produce methyl 1-isopropyl-4-methylcyclohexane carboxylate

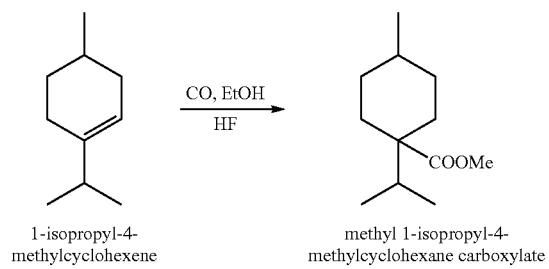

1-isopropyl-4-methylcyclohexene　　　methyl 1-isopropyl-4-methylcyclohexane carboxylate <Carbonylation Process>

The experiment was carried out by using a 500 mL stainless-steel autoclave equipped with a NAC drive-type stirrer, three inlet nozzles at the top and one outlet nozzle at the bottom which has ability to regulate internal temperature by a jacket.

Firstly, the atmosphere in the autoclave was replaced with carbon monoxide, and then, 90 g (4.5 mol) of anhydrous hydrogen fluoride was introduced therein. After regulating the liquid temperature at −30° C., the pressure was increased to 2 MPa by carbon monoxide.

Keeping the reaction temperature at −30° C. and the reaction pressure at 2 MPa, 277.5 g of the heptane solution having the 1-isopropyl-4-methylcyclohexene concentration of 32.0%, the 4-isopropyl-1-methylcyclohexane concentration of 16.1% and the heptane concentration of 51.9% which was the reaction mixture prepared in the Preparation Example 1, containing 0.64 mol of 1-isopropyl-4-methylcyclohexene, was fed into the autoclave through the top, and the carbonylation reaction was carried out. After completion of feeding, stirring was continued for approximately 10 minutes until the absorption of carbon monoxide became unobserved.

<Esterification Process>

Subsequently, keeping the reaction temperature at −30° C., 30.9 g (0.96 mol) of methanol was fed into the autoclave through the top and the esterification reaction was carried out for 1 hour under stirring.

The reaction mixture was extracted from the bottom of the autoclave into ice water, and was separated into an oil phase and a water phase. The oil phase was washed twice with 100 ml of 2% sodium hydroxide solution and twice with 100 ml of distilled water, and was dehydrated with 10 g of anhydrous sodium sulfate.

The liquid thus obtained was analyzed by gas chromatography, and as a result, it was found that a mixture having the isomer ratio of 62.8% of methyl 1-isopropyl-4-methylcyclohexane carboxylate and 37.2% of other isomers was obtained.

After removing low boiling components by an evaporator from the liquid thus obtained, rectification was carried out by a rectifier having the theoretical stage number of 20 at the distillation temperature of 139° C. under vacuum degree of 60 torr, whereby 102.9 g of a mixture of esters having the isomer ratio of 74.0% of methyl 1-isopropyl-4-methylcyclohexane carboxylate and 26.0% of the other isomers was obtained as a main fraction of distillate, wherein the yield was 59.7 mol % based on 1-isopropyl-4-methylcyclohexene.

<Carbonyl Group-Reduction Process; Production of (1-isopropyl-4-methylcyclohexyl) methanol by reducing methyl 1-isopropyl-4-methylcyclohexane carboxylate>

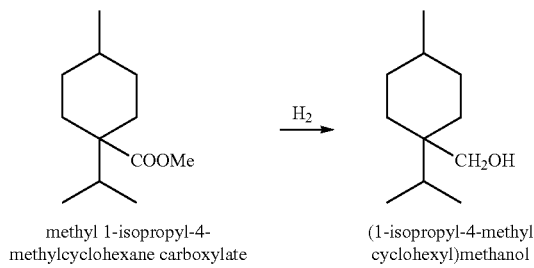

methyl 1-isopropyl-4-methylcyclohexane carboxylate (1-isopropyl-4-methyl cyclohexyl)methanol 2.5 g of Cu—Zn catalyst carried on alumina, manufactured by JGC Catalysts and Chemicals Ltd., 50.0 g of the mixture of esters obtained in the above-mentioned main fraction of distillate containing 74.00 of methyl 1-isopropyl-4-methylcyclohexane carboxylate and 26.0% of the other isomers were charged into a stainless-steel autoclave and reduction reaction was carried out by stirring for 20 hours at 260° C. under 10 MPa of hydrogen pressure while flowing hydrogen gas without the use of solvents.

After filtrating the reaction mixture to remove catalyst, 34 g of a product which was a mixture containing 73.5% of (1-isopropyl-4-methylcyclohexyl) methanol and 26.5% of the other isomers was produced, wherein the yield of (1-isopropyl-4-methylcyclohexyl) methanol was 79.2 mol % based on methyl 1-isopropyl-4-methylcyclohexane carboxylate.

After removing low boiling components by an evaporator from the mixture thus obtained, rectification was carried out by a rectifier having the theoretical stage number of 20 to isolate the main product. The fraction of distillate thus obtained had 92.0% of purity and had excellent floral-green-like fragrance with a crisp and fresh feeling.

As a result of GC-MS analysis, the molecular weight thereof was found to be 170 which was same as the molecular weight of the intended compound.

As a result of $^1$H-NMR spectrum measured in a heavy chloroform solvent, the chemical shifts (δppm, TMS standard) were found at 3.65 (br, 1H), 3.45 (s, 2H), 1.81 (m, 1H), 1.61 (m, 1H), 1.56 (m, 2H), 1.52 (m, 2H), 1.31 (m, 2H), 1.27 (m, 2H), 0.96 (d, 3H) and 0.83 (d, 6H), whereby it was identified as (1-isopropyl-4-methylcyclohexyl) methanol represented by formula (1).

Example 2

Fruit-Type Perfume Composition 5 parts by mass of the compound represented by chemical formula (1) which was obtained in Example 1 was mixed with 95 parts by mass of a perfume composition having a composition shown in Table 1, whereby a fruit-type perfume composition characterized in crisp sweetness evoking pineapple.

TABLE 1

| Component | Parts by mass |
| --- | --- |
| dimethyl benzyl carbynyl butyrate | 60 |
| dimethyl benzyl carbynyl acetate | 10 |
| benzyl butyrate | 5 |
| "FRUITATE" by Kao Corporation | 5 |
| "FLORAMAT" by Kao Corporation | 5 |

TABLE 1-continued

| Component | Parts by mass |
| --- | --- |
| benzylalcohol | 3 |
| ethylmaltol | 3 |
| γ-undecalactone | 1 |
| Vanillin | 1 |
| Vanitrope | 1 |
| Rose Type | 1 |
| Total | 95 |

INDUSTRIAL APPLICABILITY

The novel alicyclic alcohol compound of the present invention is novel in terms of having excellent floral-green-like fragrance with a crisp and fresh feeling. Because of its excellent fragrance sustaining properties, it is useful as a perfuming ingredient for a wide variety of products such as toiletry products, soaps and detergent for clothing.

In addition, the manufacturing method for producing the alicyclic alcohol compound of the present invention enables to produce said alicyclic alcohol compound by an industrially beneficial process.

The invention claimed is:

1. An alicyclic alcohol compound of formula (1):

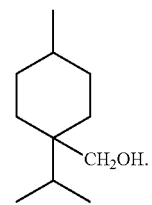

(1)

2. A perfume composition comprising the alicyclic alcohol compound of claim 1

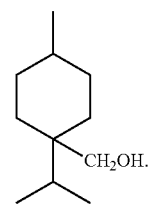

(1)

3. The alicyclic alcohol compound of claim 1, wherein said compound is in the form of the cis isomer.

4. The alicyclic alcohol compound of claim 1, wherein said compound is in the form of the trans isomer.

5. A mixture comprising molecules of the alicyclic alcohol compound of claim 1 in both the cis isomer form and the trans isomer form.

6. A mixture consisting of molecules of the alicyclic alcohol compound of claim 1 in both the cis isomer form and the trans isomer form.

7. The perfume composition of claim 2, further comprising at least one fragrance material selected from the group consisting of natural essential oils, natural extracts and synthetic perfumes of hydrocarbons, alcohols, phenols, esters, carbonates, aldehydes, ketones, acetals, ethers, nitryls, carboxylic acids, and lactones.

* * * * *